United States Patent [19]

Okita et al.

[11] Patent Number: 4,822,361
[45] Date of Patent: Apr. 18, 1989

[54] TUBULAR PROSTHESIS HAVING A COMPOSITE STRUCTURE

[75] Inventors: Koichi Okita; Shigeru Asako; Katsuya Yamada; Kazuhiro Okabe; Tohru Kashiwagi, all of Osaka, Japan

[73] Assignee: Sumitomo Electric Industries, Ltd., Osaka, Japan

[21] Appl. No.: 945,971

[22] Filed: Dec. 24, 1986

[30] Foreign Application Priority Data

Dec. 24, 1985 [JP] Japan .................. 60-296491
Dec. 24, 1985 [JP] Japan .................. 60-296492

[51] Int. Cl.$^4$ .................... A61F 2/04; A61F 2/06
[52] U.S. Cl. ................................. 623/12; 623/1
[58] Field of Search .......... 623/1, 11, 15, 16, 66, 623/12; 128/156; 264/288.8, 127

[56] References Cited

U.S. PATENT DOCUMENTS

| | | | |
|---|---|---|---|
| 3,276,448 | 10/1966 | Kronenthal | 623/1 X |
| 3,425,418 | 2/1969 | Chvapil et al. | |
| 3,953,566 | 4/1976 | Gore | 264/288.8 |
| 4,208,745 | 6/1980 | Okita | |
| 4,234,535 | 11/1980 | Okita | 264/288.8 X |
| 4,332,035 | 6/1982 | Mano | |
| 4,378,017 | 3/1983 | Kosugi et al. | 623/1 X |
| 4,399,123 | 8/1983 | Oliver et al. | 623/11 X |
| 4,713,070 | 12/1987 | Mano | 623/1 |

FOREIGN PATENT DOCUMENTS

| | | |
|---|---|---|
| 0051354 | 12/1982 | European Pat. Off. |
| 0092414 | 10/1983 | European Pat. Off. |
| 1491218 | 4/1969 | Fed. Rep. of Germany |
| 61-92672 | 5/1986 | Japan |

OTHER PUBLICATIONS

Trans. Am. Soc. Artif. Intern. Organs, vol. XXXI, pp. 107–110 (1985) by Lei et al.
Soviet Inventions Illustrated, Section C, Week J49, Jan. 1983, Abstract No. 06590, B07 A96 D22 P32.

*Primary Examiner*—Richard J. Apley
*Assistant Examiner*—Alan W. Cannon
*Attorney, Agent, or Firm*—Sughrue, Mion, Zinn, Macpeak & Seas

[57] ABSTRACT

A tubular prosthesis having a composite structure comprising (i) tubular polytetrafluoroethylene having a microfibrous structure comprising small nodes interconnected with fibrils and (ii) materials which can be absorbed by a living body wherein (a) said polytetrafluoroethylene has a greater average fibril length on the outer surface than on the inner surface, and the fibrous structure of said polytetrafluoroethylene varies continuously across the thickness of the tube wall wherein said inner surface has said fibrous structure being predominantly oriented along the axial direction and said outer surface has said fibrous structure being predominantly oriented along the concentric direction; and (b) said materials which can be absorbed by a living body are collagen, at least one of albumin and chitosan, and heparin, and are distributed in such a manner that collagen is present in the portion of the tube wall which is closest to the outer surface thereof while at least one of albumin and chitosan is present in the portion of the tube wall which is closest to the inner surface thereof, and heparin is present in the inner surface of the tube wall.

10 Claims, No Drawings

TUBULAR PROSTHESIS HAVING A COMPOSITE STRUCTURE

FIELD OF THE INVENTION

The present invention relates to a tubular prosthesis comprising a polytetrafluoroethylene (PTFE) porous tube having improved tube strength and ability to bind with body tissues. More specifically, the present invention also relates to a tubular prosthesis having a composite structure comprising PTFE with a specified fibrous structure and a material which can be absorbed by a living body.

BACKGROUND OF THE INVENTION

PTFE porous tubes made by a stretching method have been used as tubular prostheses, and many cases of the clinical application of such tubes as artificial blood vessels have been reported. Such PTFE porous tubes are superior over conventional prostheses made of knitted or woven fabrics. The stretched PTFE tube has a microfibrous structure consisting of small nodes interconnected with many thin fibrils. The diameter of the fibrils, which depends on the conditions of the stretching or drawing operations employed, can be made much smaller than the filaments in the knitted or woven fabrics. In addition, because their pore size and porosity can be freely controlled, the PTFE tubes are flexible and can be used as substitutes for tubular organs such as blood vessels with little chance of thrombus formation. In addition to these advantages, the PTFE tubes allow pseudo-intima to form on the surfaces of the internal cavities thereof without causing any damage in the surrounding tissues. For these reasons, the stretched PTFE tubes are considered to be one of the most promising prostheses for replacement of tubular organs.

Relatively large tubes having an inner diameter of 6 mm or more have been demonstrated to perform well as artificial blood vessels, but with narrower tubes having an inner diameter of 5 mm or less, growth of thrombi occuring on the inner surfaces thereof, particularly at the sites where the tubes are sutured with host blood vessels has been reported. Therefore, at the present time there are no PTFE tubes available to replace any blood vessel, particularly blood vessels having an inner diameter of less than 5 mm, more particularly as narrow as 1 to 3 mm even if the tube has the same fibril structure as the artificial blood vessels having an inner diameter of 6 mm or more.

SUMMARY OF THE INVENTION

Therefore, an object of the present invention is to provide a prosthesis having excellent compatibility with a living body, particularly to provide a tubular prosthesis excellent in compatibility even if it has an inner diameter of less than 5 mm, particularly as narrow as from 1 to 3 mm.

As the results of the extensive research made by the present inventors, the above and other objects of the present invention have been attained by a tubular prosthesis having a composite structure comprising a combination of a PTFE material having a specific fibrous structure and one or more materials which exist in important organs in a living body and which hence are absorbed by a body through metabolism. More specifically the above and the other objects of the present invention have been attained by a tubular prosthesis having a composite structure comprising (i) tubular polytetrafluoroethylene having a microfibrous structure comprising small nodes interconnected with fibrils and (ii) materials which can be absorbed by a living body wherein (a) said polytetrafluoroethylene has a greater average fibril length on the outer surface than on the inner surface, and the fibrous structure of said polytetrafluoroethylene varies continuously across the thickness of the tube wall, wherein said inner surface has said fibrous structure being predominantly oriented along the axial direction and said outer surface has said fibrous structure being predominantly oriented along the concentric direction; and (b) said materials which can be absorbed by a living body are collagen, at least one of albumin and chitosan, and heparin, and are distributed in such a manner that collagen is present in the portion of the tube wall which is closest to the outer surface thereof, while at least one of albumin and chitosan is present in the portion of the tube wall which is closest to the inner surface thereof, and heparin is present in the inner surface of the tube wall.

DETAILED DESCRIPTION OF THE INVENTION

When the surface of a fibrous structure solely made of PTFE is in contact with the blood, undesirable amounts of proteins will build up on the contacted surface. This is accompanied by cohesion of platelets and adhesion of fibrins which causes the clotting of blood to proceed until thrombi form. The thrombi are responsible for the formation of emboli in tubular prostheses with small diameters.

Heparin has the ability to retard the clotting of the blood and is used as an anticoagulant in various forms. U.S. Pat. No. 3,441,142 discloses a thin film of the reaction product of an alkali metal salt of heparin with a polymer containing quaternized nitrogen atoms. U.S. Pat. No. 3,755,218 discloses the reaction product of polyurethane with heparin. U.S. Pat. No. 3,475,410 discloses a method for forming a composite membrane surface by introducing amino groups into a cellulose film and subsequent heparinization. These references have succeeded to some extent in retarding thrombus formation but they are incapable of providing tubular prostheses suitable for long-term implantation in a living body.

In accordance with the present invention, a PTFE tube having a fibrous structure is used as a material which exhibits high resistance to blood clotting during prolonged transplantation into the body; albumin which is a construction material of the blood and/or chitosan which is a biopolymer is used to the assist in binding of heparin to the PTFE tube; and collagen which is also a biopolymer is incorporated in order to promote the penetration and growth of fibroblasts and other tissues in the transplanted PTFE tube.

The method using albumin as a heparin binder is disclosed in Japanese Patent Application (OPI) No. 118761/83 (the term "OPI" as used hereinafter means an unexamined published Japanese patent application) but does not disclose artificial tubular organs intended for long-term transplantation into the body. The use of chitosan as a heparin binder is disclosed in Japanese Patent Application (OPI) No. 89868/82 but its application is limited to catheters and renal dialyzers and no reference is made to artificial tubular organs intended for long-term transplantation. The application of collagen to the outer portion of the fibrous structure of PTFE is disclosed in Japanese Patent Application (OPI) No. 106164/80, but in this method, it is required to distribute a silicone material over the surface which is in contact with blood.

Succinylation of collagen at the surface per se as a method for preventing blood clotting is disclosed in Japanese Patent Application (OPI) No. 165854/83. Collagen can be bound to heparin by the use of protamine or protamine sulfate as shown in Japanese Patent Application (OPI) No. 180162/83. However, there is no teaching therein of a PTFE tube that has both a fibrous structure and the distribution profile of the additional components contemplated by the present invention wherein collagen is present in the portion of the tube wall which is closest to the outer surface thereof and albumin and/or chitosan is present in the portion of the tube wall which is closest to the inner surface thereof, and heparin is present only in the inner surface of the tube wall, wherein the heparin is bound to the albumin and/or chitosan.

One problem associated with the use of stretched PTFE porous tubes as tubular prostheses is that they have a tendency to be torn apart by suture needles or lines which are employed to join the tubes with a living tissues. PTFE tubes frequently tear in the axial direction probably because the microfibrous structure of PTFE is predominantly oriented in the axial direction by stretching. In order to render PTFE tubes resistant to tearing, it has been proposed that a PTFE porous tape or fibers of other materials be wrapped helically onto the tube to provide an integral body. This approach is intended to prevent the tube from tearing in the axial direction by providing the outer surface of the tube with the concentric orientation, and differs from the concept of the present invention which provides a tubular prosthesis in the form of a single tube in which the fibrous structure is oriented both in the axial and concentric directions. In accordance with the present invention, the problem of tube tearing is solved by causing the fibrous structure of PTFE to vary continuously across the wall thickness including the inner surface which is predominantly oriented in the axial direction and the outer surface which is predominantly oriented in the concentric direction. Another problem which has precluded commercial application of the conventional PTFE porous tubes is that if they are bent into a small-diameter cylinder they buckle and fail to maintain the cylindrical shape. This problem is also solved by the tubular prosthesis of the present invention which has sufficient concentric orientation in the outer surface thereof to avoid buckling upon bending. The use of the conventional PTFE porous tubes as tubular prostheses has also failed to achieve anything more than limited success because of their restricted ability to bind with the surrounding tissues. The PTFE tube of the present invention has a larger average pore size in the outer surface than in the inner surface, and this provides enhanced organization of the surrounding tissues by facilitating their ingress into the tube and subsequent binding therewith. In this respect, collagen which is present in both the interior and the outer surface of the fibrous structure of the tube is particularly effective in promoting the penetration of fibroblasts through the tube wall and promoting their growth in the tube.

The PTFE porous tube which can be used in the present invention may be produced by a method which is basically the same as the one described in Japanese Patent Publication No. 13560/67. The method comprises the step in which a mixture of an unsintered PTFE powder and a liquid lubricant is supplied into a ram extruder to extrude in a tubular form, the tube thus obtained is then stretched in the axial direction, with radial expansion being optionally achieved simultaneously or afterward, while the liquid lubricant is or is not removed from the tube; thereafter while the stretched tube is fixed to prevent shrinkage, the stretched tube is sintered by heating to a sintering temperature of 327° C. or more to fix the stretched structure.

Examples of the liquid lubricant used in the present invention include those described in Japanese Patent Publication No. 13560/67.

The resulting PTFE porous tube provided with increased strength has a microfibrous structure comprising small nodes interconnected with many thin fibrils. The diameter and length of the fibrils and the size and number of the nodes can be varied by changing the conditions of stretching and sintering operations, and thus the pore size and porosity of the porous tube thus obtained can be freely controlled. It has been clinically reported that when this type of porous tube is used as an artificial blood vessel, it preferably has an average pore size of from 1 to 100 micrometers, a porosity of 70% or more, and a tube wall thickness of from 0.3 to 1.0 mm.

The PTFE porous tube produced by the method described above is typically characterized in that the fibrous structure of PTFE is predominantly oriented in the axial direction. In accordance with the present invention, the stretched tube is sintered, while being fixed to prevent thermal shrinkage, by heating the outer surface of the tube to a temperature of 327° C. or higher until it acquires a meshed or network-like structure. By this process, the outer surface of the tube attains a larger average pore size than the inner surface and the fibrous structure of PTFE is caused to vary continuously across the wall thickness from the inner surface which is predominantly oriented along the axial direction to the outer surface which is predominantly oriented along the concentric direction. The present invention offers this PTFE porous tube as a tubular prosthesis.

The outer surface of the tube is provided with a meshed or network-like structure by heating the tube from outside to a temperature of 327° C. or higher. As the tube is heated to such elevated temperature, the fibrils in the outer surface of the PTFE tube increase in diameter because of the cutting or coalescing of the microfibrils and the coalescing of the nodes. This causes a corresponding increase in the pore size, or the diameter of the gap between adjacent fibrils. The higher the temperature at which the outer surface of the tube is maintained and the longer the period during which it is maintained at temperatures higher than 327° C., the more pronouncedly the phenomenon described above occur, and the outer surface of the tube will eventually attain a network-like structure having pore sizes of from several tens micrometers to several millimeters. This change in fibrous structure will proceed into the tube wall, provides a smooth pore size gradient through the wall thickness from the inner surface to the outer surface. The fibrous structure of the outer surface of the PTFE porous tube thus produced is highly oriented along the concentric direction, and is transverse to the axial direction along which the fibril structure of the tube has been oriented as a result of the stretching.

As described above, by appropriately controlling the temperature and time conditions to be employed for sintering operations, the PTFE tube can be provided with a gradual profile of change in its fibrous structure through the thickness of the tube wall wherein the porous structure of the inner surface is predominantly oriented along the axial direction and that of the outside surface is highly oriented along the concentric direction. One characteristic of the present invention is to allow the stretched PTFE tube to be sintered to a far greater extent than has been achieved with the conventional PTFE sinters.

The tublar prosthesis of the present invention preferably has an average fibril length of the outer surface thereof which is at least 5 times, more preferably at least 10 times, that of the inner surface. The thickness of the nodes in the outer surface of the tublar prosthesis of the present invention is preferably at least 10 times that of the inner surface.

In order for the tubular prosthesis of the present invention to be used as an artificial blood vessel, the average pore sizes in the inner and outer surfaces of the PTFE porous tube are preferably within the ranges of from 1 to 100 micrometers and from 0.1 to 1.0 mm, respectively, and these pore size ranges could be easily attained by the present invention. The tubular prosthesis of the present invention is possessed of such improved characteristics that it is highly resistant to tearing and buckling. In addition, the prosthesis has an improved ability to bind with the tissues of a living body because of the presence of the pores which provide passages for the penetration of the surrounding tissues.

The porosity of the PTFE porous tube used in the present invention is preferably from 70 to 90%, more preferably from 75 to 85%.

Other materials of the tubular prosthesis of the present invention which can be absorbed by a living body are described below.

Collagen is present in an amount of about 25 wt % in skins, hides, tendons, bones, and soft bones of the animal body. Collagen is also present in the blood vessels and heart of an animal in amounts of from 5 to 10 wt %. Collagen is obtained by first decomposing the fat tissues of calf skin with an appropriate enzyme such as lipase, then digesting the antigenic polypeptide portion with an appropriate enzyme such as pepsin. The temperature is critical to these procedures since if soluble collagen obtained is heated to a temperature higher than the melting point, which is between 40° C. and 50° C., it is converted to gelatin as a result of breakdown of the triple-stranded helical conformation of the three polypeptide strands in collagen. However, even the gelatin formed as a result of thermal denaturation has some capabilities similar to those of collagen, so that partially gelatinized collagen can be employed. It should however be emphasized that collagen without thermal denaturation is particularly preferred.

Albumin is made of globular proteins present in the plasma component of the blood in a concentration of as high as 4 to 5 g/dl. Albumin serves to maintain the osmotic pressure of the blood and to transport various substances in the blood. Being highly soluble in water, albumin is selectively adsorbed on hydrophilic sites of high molecular weight substances which are in contact with the blood, and this may be compared with the fact that γ-globulins relating to immune reactions are insoluble in water and are adsorbed on hydrophobic sites of the blood-contacting high molecular weight substances.

Heparin is present in liver, lung, intestines and skin, and is a polysaccharide wherein hydroxy groups in the cellulose structure are substituted by aminosulfate groups or sulfate esters. Heparin is known to be the most potent anticoagulant.

Chitosan is made from chitin which is derived from the exoskeletons of insects and crustaceans, and a part of the hydroxy groups in the cellulose structure thereof is substituted by acetamido groups. Chitosan is made by deacetylating the acetamido groups in chitin with alkali and is characterized by the presence of primary amino groups.

The composite structure contemplated by the present invention may be attained by, for example, the following procedures. First, a fibrous structure of PTFE in a tubular form having a predetermined inner diameter is submerged in an aqueous solution of albumin and dried under reduced pressure. Subsequently, the tube is submerged in an aqueous solution of collagen and dried under reduced pressure. The outer surface of the tube is then applied with a collagen solution and dried. The inner surface of the tube is subsequently applied with a mixed solution of albumin and heparin and dried at room temperature. The biopolymers in the resulting composite structure, that is albumin, collagen, and heparin, are crosslinked by the treatment with an aqueous solution of a dialdehyde compound (e.g., glutaraldehyde, dialdehyde starch, glyoxal, etc.) so that they becomes water-insoluble.

Another method for attaining the composite structure starts with a fibrous structure of PTFE in a tubular form having a predetermined inside diameter which is submerged in an aqueous solution of chitosan and dried under reduced pressure; then the tube is submerged in an aqueous solution of collagen and dried under reduced pressure; the outer surface of the tube is applied with a collagen solution and dried; the inner surface of the tube is subsequently applied with a mixed solution of chitosan and heparin and dried at room temperature. As in the first method, the biopolymers in the resulting composite structure, that is chitosan, collagen, and heparin, are crosslinked by treatment with an aqueous solution of a dialdehyde compound (e.g., glutaraldehyde, dialdehyde starch, glyoxal, etc.) so that they becomes insoluble in water.

The process for producing the composite structure of the present invention allows for a fairly large latitude in selecting the order of applying and impregnating, the biopolymers so long as the intended laminar structure is imparted to the wall of the PTFE tube. For instance, the PTFE tube is first impregnated with a mixed solution of albumin and/or chitosan and collagen, then applied on the inner surface with albumin and/or chitosan, followed by heparin applying, and finally the outer surface of the tube is applied with collagen. In another approach, the tube is first impregnated with a solution of albumin and/or chitosan, applied on the outer surface with collagen, and finally applied on the inner surface with heparin. The biopolymers may be impregnated or applied by impregnation under vacuum or injection under pressure.

The biopolymers may be acidic or alkaline, in order to attain higher solubilities to water or physiological saline solution. The solutions of biopolymers generally have concentrations within the range of from 0.05 to 10 wt % but collagen may be dissolved at a concentration of as high as 20 wt %. In order to permit the biopolymers to be uniformly impregnated in the bulk of the fibrous structure of PTFE or to be applied uniformly on its surface, it is preferred that the PTFE tube be first washed with an appropriate solvent such as alcohol, then washed with water and impregnated with the biopolymers at a concentration of from 0.1 to 5 wt %. The duration of the period during which the PTFE tube is submerged in biopolymer solutions may range from 1 to 10 minutes but, if the fibrous structure cf PTFE is compressed with an appropriate means such as rollers, the period can be reduced to less than 1 minute without sacrificing the uniformity of impregnation cf the biopolymers. The applied biopolymers may be adequately crosslinked by submerging the tube within an aqueous solution of a dialdehyde compound having a concentration of from 0.05 to 0.5%, preferably from 0.2 to 0.5%, for a period of from 1 minute to 48 hours.

While, as discussed above, the tubular prosthesis of the present invention is highly useful as an artificial blood vessel, it is also useful as a replacement for other tubular organs such as the esophagus, tracchea, bile duct, ureter and urethra.

The following examples are provided for the purpose of further illustrating the advantages of the present invention but are in no way to be taken as limiting the scope of the invention. Unless otherwise indicated, all parts, ratios, and percents are by weight.

EXAMPLE 1

Preparation of poros PTFE tube

A hundred parts by weight of a fine PTFE powder (Polyflon F-104E produced by Daikin Kogyo Co., Ltd.) was intimately mixed with 29 parts by weight of a liquid lubricant (DOSB produced by Shell Chemical Co., Ltd., containing 99.98 vol % of paraffin). The mixture was shaped into a preform, and then supplied into a ram extruder to extrude a tubular form having an inner diameter of 3.0 mm and an outer diameter of 4.5 mm. The tube thus-obtained was submerged in trichloroethylene to extract the liquid lubricant. The tube was stretched 300% in the axial direction while being heated at about 250° C. The thus-stretched tube was heated at about 330° C. and inflated by applying vacuum onto the outer surface thereof so as to make the porous PTFE tube having an inner diameter of 4.0 mm. A stainless steel rod with a diameter of 4.0 mm was inserted through the tube, and then the tube was heated at 350° C. for 30 minutes with both ends fixed to the rod. After being cooled to room temperature, the steel rod was withdrawn from the tube which had assumed an inner diameter of 4.0 mm, an outer diameter of 4.9 mm, a porosity of 80%, and average pore sizes of 2.0 micrometers and 0.15 mm on the inner and outer surfaces, respectively. A stainless steel wire having a diameter of 0.4 mm was pierced through the tube wall at a distance of 5 mm from one end of the tube and both ends of the wire were joined to form a loop. When the loop was pulled along the axial direction at a rate of 50 mm/min, the tube did not tear until the load increased to 3,800 g, which was significantly greater than 180 g correspond the tear strength of a PTFE porous tube prepared by the conventional sintering method. Because of this remarkable improvement in tear strength, the tube could be sutured with blood vessels in a host body with little chance of tearing in the longitudinal direction.

EXAMPLE 2

Preparation of Collagen Solution

Calf skin was broken into small pieces and mixed with HCl to attain a pH of 3. About 1 wt % of pepsin based on the amount of collagen contained in the calf skin was added to the mixture and agitated for 4 to 5 days at room temperature. The viscous collagen solution thus-obtained was neutralized with NaOH to attain a pH of 7 to 8, whereupon a collagen precipitate formed. The precipitated collagen was collected by centrifugation, washed with water and dissolved in 0.5M NaCl in a concentration of 0.5 wt %.

EXAMPLE 3

Preparation of Albumin Solution

Human serm albumin was dissolved in a 0.2M phosphate buffer (pH: 7.4) for a concentration of 0.3 wt %. In order to achieve uniform impregnation in the hydrophobic PTFE porous tube, the albumin solution was placed in a capillary equiped with a cock connected to a vacuum line. The capillary was also equipped at the bottom with a cock for providing a passage through which the albumin solution could be discharged and the phosphate buffer introduced.

EXAMPLE 4

Preparation of Chitosan Solution

A crab shell was broken into small pieces and agitated in 2N HCl for 3 days to extract the soluble components. The insoluble components were heated with agitation in 1N NaOH to extract any residual soluble components. The insoluble components were dried and heated to 180° C. under nitrogen in the presence of 5 times volume of NaOH. Alkali fusion occurred and thus chitin was deacetylated to produce chitosan. The precipitate was washed with water and dissolved in a 1% acetic acid solution for a chitosan concentration of 1.2 wt %.

EXAMPLE 5

Preparation of Mixed Solution of Collagen and Albumin

The collagen solution prepared in Example 2 and the albumin solution prepared in Example 3 were slowly mixed at a temperature not higher than 5° C. Any fibrous precipitate forming in a trace amount was dissolved by the addition of 0.05N HCl.

EXAMPLE 6

Preparation of Mixed Solution of Collagen and Chitosan

The collagen solution prepared in Example 2 and the chitosan solution prepared in Example 4 were slowly mixed at a temperature not higher than 5° C. Any fibrous precipitate forming, in a trace amount was dissolved by the addition of 0.1N HCl.

EXAMPLE 7

Preparation of Mixed Solution of Albumin and Heparin

To the albumin solution prepared in Example 3, heparin sodium salt as dissolved in a 0.2M phosphate buffer (pH: 7) was added dropwise so as to form a solution wherein the amino groups in albumin were ionically bound to the sulfate groups in heparin.

EXAMPLE 8

Preparation of Mixed Solution of Chitosan and Heparin

To the chitosan solution prepared in Example 4, heparin sodium salt as dissolved in a 0.2M phosphate buffer (pH: 7) was added dropwise so as to form a solution wherein the amino groups in chitosan were ionically bound to the sulfate groups in heparin.

EXAMPLE 9

Application onto the Inner Surface of PTFE Tube

The porous PTFE tube prepared in Example 1 was submerged in the mixed solution prepared in Example 5. In order to allow the solution to be uniformly impregnated in the porous structure of the PTFE tube, the tube was subjected to at least three cycles of evacuation and pressurization while it was immobilized in the solution. Thereafter, the tube was left to stand at 20° C. for 12 hours. After the mixed solution was discharged, the tube was dried under reduced pressure at room temperature, washed with 0.02N NaOH, then with a 0.2M phosphate buffer.

EXAMPLE 10

Application onto the Outer Surface of PTFE Tube

The outer surface of the PTFE porous tube prepared in Example 9 was applied with the collagen solution prepared in Example 2. The tube was thereafter dried under reduced pressure and then washed with distilled water.

Better results are attained in Examples 9 and 10 if the treatments of the PTFE porous tube are conducted with a stainess steel rod being inserted through the tube as in Example 1. The two particular advantages resulting from the use of a stainless steel rod are (i) a PTFE tube having a small specific gravity can be immobilized in the biopolymer solution even if the interior of the tube is maintained under vacuum; and (ii) uniform application can be conducted to the outer surface of the tube by applying the collagen solution over a given period while rotating the stainless steel rod with the both ends thereof being fixed.

EXAMPLE 11

Application onto the Inner Surface of PTFE tube and Crosslinking with Dialdehyde The mixed solution of albumin and heparin prepared in Example 7 was applied onto the inner surface of the PTFE porous tube prepared in Example 10. Before the application, the stainless steel rod had been withdrawn from the PTFE tube. A syringe charged with the mixed solution of albumin and heparin was connected to the PTFE tube and the solution was introduced at 20° C. for a period of 2 to 20 hours (preferably 5 hours) such that it would contact only the inside surface of the tube. Thereafter, the tube was submerged within a 0.3% dialdehyde starch solution at 25° C. for 20 minutes, and dried under reduced pressure.

EXAMPLE 12

Application onto the Inner Surface of PTFE Tube

The porous PTFE tube prepared in Example 1 was submerged in the mixed solution prepared in Example 6. In order to allow the solution to be uniformly impregnated in the porous structure of the PTFE tube, the tube was subjected to at least three cycles of evacuation and pressurization at 20° C. while immobilized in the solution. Thereafter, the mixed solution was discharged and the tube was dried under reduced pressure at room temperature, washed first with 0.1N NaOH, then with distilled water.

EXAMPLE 13

Application onto the Outer Surface of PTFE Tube

The outer surface of the PTFE tube prepared in Example 12 was applied with the collagen solution prepared in Example 2 at 20° C. for 1 hour. The tube was thereafter dried under reduced pressure and washed with distilled water. For the same reasons as given in connection with Examples 9 and 10, better results are attained in Examples 12 and 13 by treating the PTFE tube with a stainless steel rod being inserted through the tube.

EXAMPLE 14

Application onto the Inner Surface of PTFE Tube and Crosslinking with Glutaraldehyde The mixed solution of chitosan and heparin prepared in Example 8 was applied onto the inner surface of the PTFE porous tube prepared in Example 13. Before the application, a stainless steel rod had been withdrawn from the PTFE tube. A syringe charged with the mixed solution of chitosan and heparin was connected to the PTFE tube and the solution was introduced at 20° C. for a period of 2 to 20 hours (preferably 5 hours) such that it would contact only the inner surface of the tube. Thereafter, the tube was submerged within a 0.1% glutaraldehyde solution at 25° C. for 10 hours, and dried under reduced pressure.

EXAMPLE 15

A porous PTFE tube was prepared in the same manner as in Example 1 except that the unsintered PTFE tube having an inner diameter of 2.0 mm was expanded to 3.0 mm by sintering. By the same manner as in Examples 9 to 11, a tubular prosthesis having an inside diameter of 3.0 mm was fabricated.

EXAMPLE 16

The PTFE tube prepared in Example 1 was submerged in a 2% aqueous solution of poly(oxyethylene nonylphenyl ether) and subsequently dried. The tube was submerged in the solution prepared in Example 3, and dried thereafter. The outer surface of the tube was applied with the solution prepared in Example 2. After withdrawing the stainless steel rod from the tube, the solution prepared in Example 7 was supplied onto only the inner surface thereof, which was thereafter washed with a phosphate buffer. The tube was subjected to crosslinking by submerging within a 0.2% aqueous solution of glutaraldehyde at 25° C. for 8 hours, and finally washed with a phosphate buffer.

The PTFE tubes prepared in Examples 11, 14, 15 and 16 were found to have superior characteristics that made them highly suitable for use as artificial blood vessels.

While the invention has been described in detail and with reference to specific examples thereof, it will be apparent to one skilled in the art that various changes and modifications can be made therein without departing from the spirit and scope thereof.

What is claimed is:

1. A tubular prosthesis having a composite structure comprising
   (i) tubular polytetrafluoroethylene having a microfibrous structure comprising small nodes interconnected with fibrils and
   (ii) materials which can be absorbed by a living body
   wherein (a) said polytetrafluoroethylene has a greater average fibril length on the outer surface than on the inner surface, and the fibrous structure of said polytetrafluoroethylene varies continuously across the thickness of the tube wall wherein said inner surface has said fibrous structure being predominantly oriented along the axial direction and said outer surface has said fibrous structure being predominantly oriented along the concentric direction; and (b) said materials which can be absorbed by a living body are collagen, at least one of albumin and chitosan, and heparin, and are distributed in such a manner that collagen is present only in the portion of the tube wall which is closest to the outer surface thereof or the outer surface of the tube wall while at least one of albumin and chitosan is present only in the portion of the tube wall which is closest to the inner surface thereof or the inner surface of the tube wall, and heparin is present only in the inner surface of the tube wall.

2. A tubular prosthesis having a composite structure as in claim 1, wherein the outer surface of said tubular polytetrafluoroethylene has an average fibril length which is at least 5 times that of the inner surface.

3. A tubular prosthesis having a composite structure as in claim 2, wherein the outer surface of said tubular polytetrafluoroethylene has an average fibril length which is at least 10 times that of the inner surface.

4. A tubular prosthesis having a composite structure as in claim 1, wherein the nodes in the outer surface of said tubular polytetrafluoroethylene have a thickness which is at least 10 times that of nodes in the inner surface.

5. A tubular prosthesis having a composite structure as in claim 1, wherein said collagen has been freed of any antigenic groups by the treatment with pepsin and has been crosslinked with glutaraldehyde or dialdehyde starch.

6. A tubular prosthesis having a composite structure as in claim 1, wherein said chitosan has been crosslinked with glutaraldehyde or dialdehyde starch.

7. A tubular prosthesis having a composite structure as in claim 1, wherein said tubular prosthesis has an inner diameter of 5 mm or less.

8. A tubular prosthesis having a composite structure as in claim 7, wherein said tubular prosthesis has an inner diameter of from 1 to 3 mm.

9. A tubular prosthesis having a composite structure as in claim 1, wherein said tubular polytetrafluoroethylene has a porosity of from 70 to 90%.

10. A tubular prosthesis having a composite structure as in claim 9, wherein said tubular polytetrafluoroethylene has a porosity of from 75 to 80%.

* * * * *